(12) United States Patent
Muennig et al.

(10) Patent No.: US 7,041,858 B1
(45) Date of Patent: May 9, 2006

(54) PROCESS FOR THE PRODUCTION OF DINITROTOLUENE

(75) Inventors: Juergen Muennig, Kaarst (DE); Bernd Pennemann, Bergisch Gladbach (DE); Dietmar Wastian, Dormagen (DE); Volker Michele, Cologne (DE); Jesse Caravaggio, Kingwood, TX (US); John F. Gisch, Jr., Houston, TX (US)

(73) Assignees: Bayer MaterialScience LLC, Pittsburgh, PA (US); Bayer MaterialScience AG, Leverkusen (DE)

( * ) Notice: Subject to any disclaimer, the term of this patent is extended or adjusted under 35 U.S.C. 154(b) by 0 days.

(21) Appl. No.: 11/054,012

(22) Filed: Feb. 9, 2005

(51) Int. Cl.
*C07C 205/00* (2006.01)
(52) U.S. Cl. .................. 568/927; 934/936; 934/939
(58) Field of Classification Search ........... 568/937, 568/934, 936, 939
See application file for complete search history.

(56) References Cited

U.S. PATENT DOCUMENTS

| | | | |
|---|---|---|---|
| 4,973,770 A | 11/1990 | Evans | 373/929 |
| 5,616,818 A | 4/1997 | Pirkl et al. | 708/932 |
| 5,763,697 A | 6/1998 | Hermann et al. | 195/939 |
| 5,902,910 A | 5/1999 | Mazzafro et al. | 903/934 |

*Primary Examiner*—J. Parsa
(74) *Attorney, Agent, or Firm*—Joseph C. Gil; N. Denise Brown

(57) ABSTRACT

The present invention is directed to a process for the isothermal nitration of aromatic organic compounds, wherein an aromatic organic compound is brought into contact and reacted with a mixture of sulfuric acid and nitric acid. The mixture of sulfuric acid and nitric acid, and the aromatic organic compound are brought into contact with each other through a mixing nozzle which comprises a substantially cylindrical tubular reactor and an annular gap which surrounds the tubular reactor. The aromatic organic compound flows through the tubular reactor, and the mixture of sulfuric acid and nitric acid flows through the annular gap, and they are mixed together upon emerging from the tubular reactor and the annular gap, wherein the ratio of the average rates of flow of the aromatic organic compound in the tubular reactor, and of the mixture of sulphuric acid and nitric acid in the annular gap ranges from 0.5:1 to 10:1.

5 Claims, 2 Drawing Sheets

PROCESS FOR THE PRODUCTION OF DINITROTOLUENE

BACKGROUND OF THE INVENTION

The present invention relates to a process for the nitration of aromatic organic compounds in the liquid phase, wherein the aromatic organic compound is intensively mixed with a mixture of nitric acid and sulfuric acid in a mixing nozzle, and fed to a reactor with active mixing. In a variation of this process, dinitrotoluene is produced from toluene.

Dinitrotoluene (DNT) is an intermediate from the production of toluene diisocyanate (TDI). DNT can be produced on an industrial scale by the nitration of toluene with nitric acid in the presence of sulfuric acid (see Ullmann's Encyclopedia of Industrial Chemistry, $6^{th}$ Edition, 2003, Wiley). The disadvantage of this process, however, is that the waste water that is obtained typically has to be cleaned before it can be discharged into surface water as waste water. It is relatively expensive to clean this waste water.

Accordingly, an object of the present invention is to reduce the formation of these secondary products that end up in the waste water, and hence, reduce the cost for cleaning the waste water.

The nitration of aromatics substantially takes place in the aqueous of the two phases. In order to react with one another, the components of the organic phase, such as, for example, toluene, must diffuse through the interface between the two phases to react in the aqueous phase in the presence of sulfuric acid with the nitric acid that is present there in excess. In such cases it is known that, depending on the reaction conditions, the effective speed of the reaction may depend greatly on the size of the phase interface. The size of this interface can be increased by intensive stirring, for example, which has an advantageous effect on the reaction speed. Other factors that influence the reaction speed include the reaction temperature, the concentrations in the organic phase of the components to be reacted and concentrations of the nitric acid and sulfuric acid in the aqueous phase. As the reaction proceeds, the water formed during nitration will dilute the sulfuric acid, thereby reducing the reaction speed. The reduction in the nitric acid concentration due to its consumption in the reaction also helps to reduce the reaction speed.

If the reaction is controlled appropriately, these dependencies can be used to control the nitration of the organic compounds in the organic phase but only to a certain level. For example, with an appropriate choice of temperature and sulfuric acid concentration in the waste acid, the nitration of toluene will proceed as far as mononitrotoluene (MNT) only, largely preventing the formation of DNT. In the same way, the formation of trinitrotoluene (TNT) can largely be prevented in the nitration of toluene to DNT.

It is also known that, under appropriate conditions, nitric acid is capable not only of nitrating but also of oxidizing the organic compounds. Possible compounds obtained by the oxidation of toluene, MNT or DNT are cresols, phenols and nitration products thereof. A low sulfuric acid concentration increases the oxidation tendency of nitric acid, so the content of organic secondary products in the reaction mixture will increase as the sulfuric acid concentration is reduced. This can lead to a lower limit of sulfuric acid concentration at which this process is economically viable.

Dinitrotoluene is conventionally produced in a continuous process, so the concentrations and temperatures in the reactors can largely be kept constant over time. Stirred-tank reactors or series of stirred-tank reactors, loop reactors and tubular reactors of various sizes, which in some cases have internal fittings, can be also used, for example. The thorough mixing that is required for the reaction can be achieved in various ways. If tubular reactors are used for the nitration, the use of mixing nozzles to achieve the thorough mixing is known and is described in, for example, EP-A-0373 966 or in DE-A-195 39 205. The mononitration of benzene that is described there, however, is not transferable to the dinitration of toluene. This is because in the nitration of toluene, the mixture obtained breaks down into the two phases again before the reaction is completed. For that reason, as described in, for example, EP-A-708 076, several of these mixing devices are used in series in the direction of flow. Although in the isothermal process, this leads to difficulties because of the heat exchangers that are needed to dissipate the reaction heat. For that reason, reactors with active mixing are used in the isothermal process. In the case of tubular reactors, circulating pumps can be used, in which case part or all of the recirculated stream is returned to the entrance of the reactor. In the case of stirred- tank reactors, as described in, for example, EP-A-903 336, thorough mixing is typically achieved through the use of a suitable agitator. The goal of having as selective a reaction as possible and widespread prevention of the formation of secondary products is not achieved through the use of the cited reactors alone, however.

Thus, the object of the present invention is to provide a simple and economic process for the nitration of organic compounds in which the formation of secondary products can largely be prevented.

SUMMARY OF THE INVENTION

The present invention is directed to a process for the isothermal nitration of aromatic organic compounds. This process comprises (A) contacting (1) an aromatic organic compound, with (2) a mixture of (a) sulfuric acid and (b) nitric acid, and (B) reacting the mixture of (1) aromatic organic compound and (2) the mixture of (a) sulfuric acid and (b) nitric acid, thereby forming nitrated aromatic organic compounds. In step (A) where (1) the aromatic organic compound and (2) the mixture of (a) sulfuric acid and (b) nitric acid are brought into contact with one another, this is achieved through a mixing nozzle, which comprises a substantially cylindrical tubular reactor and an annular gap surrounding the tubular reactor. Component (1), the aromatic organic compound, flows through the tubular reactor, and component (2) the mixture of (a) sulfuric acid and (b) nitric acid flows through the annular gap, and these are mixed together on emerging (respectively) from the tubular reactor and the annular gap. The ratio of the average rates of flow (unit: m/s) of (1) the aromatic organic compound in the tubular reactor, and of (2) the mixture of (a) sulfuric acid and (b) nitric acid in the annular gap ranges from 0.5:1 to 10:1.

DETAILED DESCRIPTION OF THE INVENTION

Figure 1:
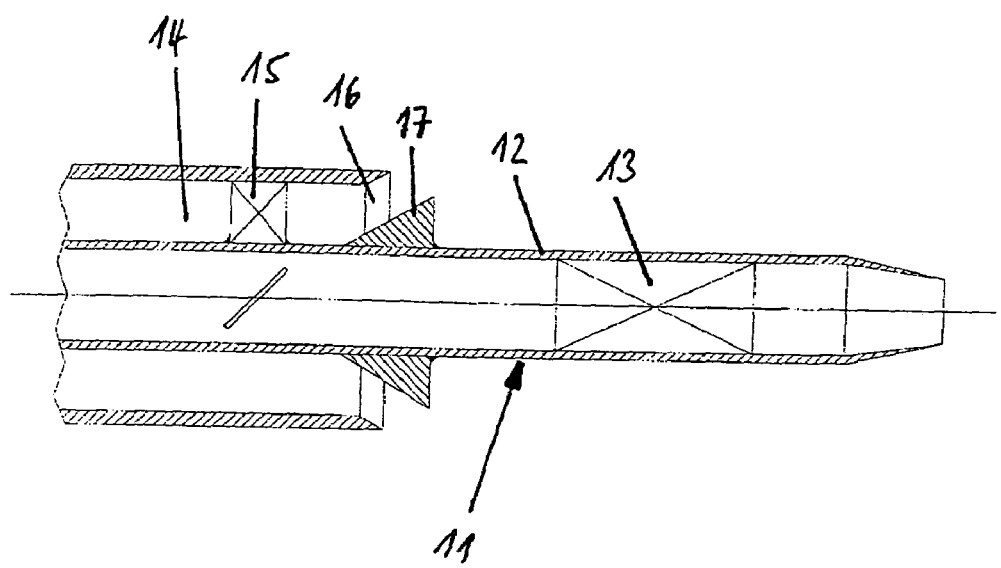
FIG. 1 is a cross-sectional view of a suitable mixing nozzle for mixing the aromatic organic compound and the mixture of sulfuric acid and nitric acid.

As the aromatic compound leaves the substantially cylindrical tubular reactor, the aromatic organic compound is enveloped by the mixture of sulfuric acid and nitric acid, and is then mixed with it. Then, the reaction mixture is preferably injected into a reactor with active mixing, or in other words, a reactor fitted with a mixing device, such as, for example, a stirred container or a container provided with a circulating pump. Nitric acid and sulfuric acid are preferably premixed before entering the mixing nozzle to produce the nitrating acid. This is necessary to prevent the development of areas of high nitric acid concentration and low sulfuric acid concentration, or low nitric acid and high sulfuric acid concentration.

In a preferred embodiment of the process, the stream of aromatic organic compound in the tubular reactor is set in rotary motion by internal fittings such as, for example, a helix, and/or the stream of the mixture of sulfuric acid and nitric acid in the annular gap is set in rotary motion by internal fittings such as, for example, inclined deflection plates, to further increase the mixing speed. An even greater improvement of the mixing process is achieved if the nozzle outlet has a conical flow profile, thereby additionally causing a rapid mixing with the remaining reactor contents. Both measures also lead to the formation of small droplets of organic phase, which also has an advantageous effect on the speed and selectivity of the reaction.

In the process according to the invention, average droplet sizes of 10 to 500 µm are preferably produced, and more preferably of 20 to 200 µm.

A reactor with active mixing is preferably used in the process according to the invention. This can be, for example, a stirred-tank reactor with agitator, or a tubular reactor with circulating pump and recycling. It is advantageous here to install the mixing nozzle in the vicinity of the mixing device, with an arrangement in the suction area of the mixing device being particularly preferred.

According to the invention, a ratio of the average flow rates (unit: m/s) of organic phase (i.e. the phase containing the aromatic organic compound) to inorganic phase (i.e. the phase containing the mixture of sulfuric acid and nitric acid) of about 0.5:1 to about 10:1, and preferably of about 1.5:1 to about 5:1, is established. Furthermore, Reynolds numbers of >10,000, and preferably >50,000, are advantageously established during passage through the annular gap or the tubular reactor in the mixing nozzle. The nozzle dimensions can be defined in a manner known to the person skilled in the art, taking into account the production capacity. For conventional technical installations, flow rates of 0.3 to 10 m/s are preferably obtained. Therefore, the preferred nozzle diameters for the organic phase are about 0.3 to about 10 cm, and the preferred equivalent diameters for the acid phase are about 0.4 to about 20 cm.

If a tubular reactor with circulating pump and recycling is used as the nitration reactor, a ratio of the average flow rates of inorganic phase (which flows through the annular gap in the mixing nozzle) to recirculated reaction mixture of 0.5:1 to 10:1 is preferably established, and more preferably of 1.5:1 to 5:1.

In the process according to the invention, the organic phase and aqueous phase are preferably added in a volume ratio of 1:1 to 1:20, preferably 1:2 to 1:10. In a preferred embodiment of the process, mixed acid (nitrating acid, mixture of sulfuric acid and nitric acid) in a composition containing 5 to 10 wt. % of nitric acid, 60 to 80 wt. % of sulfuric acid and proportions of water, and optionally proportions of other substances is used, in which the combined wt. %'s of nitric acid and sulfuric acid, and the proportions of water and other substances totals 100 wt. % of the composition.

Benzene, toluene, mononitrotoluene, phenol and/or the corresponding chlorinated compounds are preferably used as the aromatic organic compound. Toluene and mononitrotoluene are more preferably used as the aromatic organic compound.

In the isothermal process of the present invention for the nitration of toluene, a mixture of isomers comprising various mononitrotoluenes (MNT) with certain proportions of DNT is conventionally first obtained from the reaction of toluene with nitric acid in the presence of sulfuric acid. The nitric acid is conventionally added here in a molar ratio of 1.01:1 to 1.15:1, relative to the organic compound (e.g. toluene) to be nitrated. In the process according to the present invention, the nitrating acid which contains nitric acid, sulfuric acid and water, is brought into contact and mixed with toluene through the mixing nozzle. The reaction mixture that is obtained is a two-phase system. The reaction heat that is generated is dissipated by cooling, the reaction temperature here is preferably 30 to 65° C. The reaction temperature and acid concentration have a known influence on the isomer distribution in the reaction product formed, which can advantageously be used to steer the composition of the reaction product in the direction of the desired isomers.

After phase separation, the aqueous phase, which preferably contains 60 to 80 wt. % of sulfuric acid, as well as residues of unreacted nitric acid and certain proportions of dissolved organic compounds such as, for example, MNT and DNT, is concentrated again. The reaction product, which predominantly consists of MNT and proportions of DNT and secondary nitration products, such as cresols and benzoic acids of varying degrees of nitration, for example, is reacted to yield DNT in a second stage. To this end, sulfuric acid and nitric acid are added once again. The nitric acid here is also conventionally used in excess, in order to achieve an almost complete reaction of the MNT. In the process according to the invention, the nitrating acid which contains nitric acid, sulfuric acid and water, is again preferably brought into contact and mixed with the reaction product from the first nitration stage, which contains MNT and DNT, through the mixing nozzle. This reaction can be performed with continuous cooling at temperatures of, for example, preferably 60 to 80° C., but can also be performed adiabatically, as described in, for example, U.S. Pat. No. 5,689,018, the disclosure of which is hereby incorporated by reference.

The reaction product obtained is then conventionally separated into phases again. The resultant aqueous phase that is obtained which consists largely of sulfuric acid and residues of nitric acid, together with dissolved organic components, is preferably reused in the mononitration. The organic product that is obtained, which consists largely of DNT but can also contain impurities such as dissolved amounts of sulfuric acid, nitric acid and organic secondary products such as, for example, cresols and benzoic acids of varying degrees of nitration and possibly also small amounts of MNT, is conventionally sent for washing. Here, some of the cited impurities are removed and converted to the aqueous phase, to yield purified DNT.

Reference will now be made to the figures to further explain and describe the invention.

FIG. 1 illustrates the cross-section of a suitable design for the mixing nozzle. In the mixing nozzle 11 as shown in FIG. 1, the rotary motion is achieved in the tubular reactor 12 by means of a helix 13 and in the annular gap 14 by means of inclined deflection plates 15. The annular exit gap 16 for the nitrating acid is directed outwards with the aid of a cone 17 in order to obtain a conical flow profile.

Figure 2:
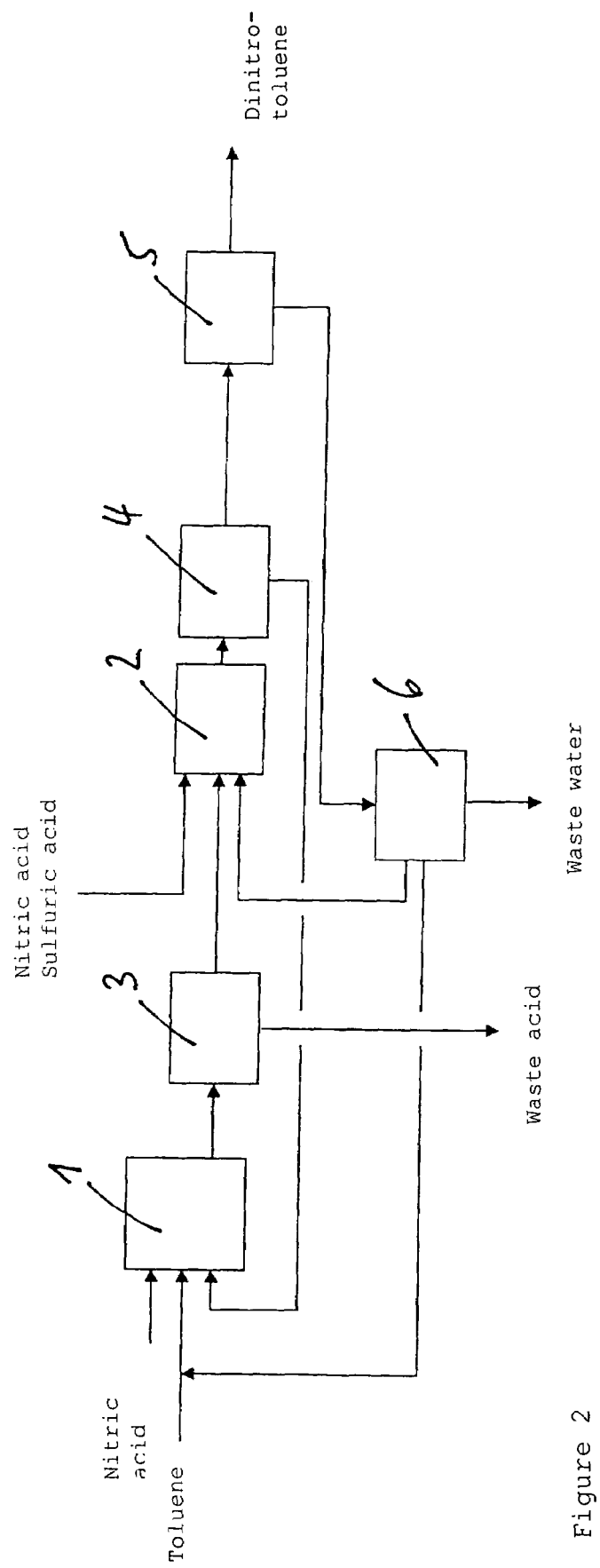
FIG. 2 illustrates a suitable flow diagram of a plant for the production of dinitrotoluene.

FIG. 2 illustrates a flow diagram of a suitable plant for the production of dinitrotoluene. The mixing nozzle illustrated in FIG. 1 (but not shown in FIG. 2) is used in an industrial plant for producing dinitrotoluene such as that shown in FIG. 2. As shown in the flow diagram, the plant contains reactors 1 and 2 that may be equipped with agitators and heat exchangers (not shown), phase separating units 3 and 4, a product washing unit 5 and a waste water treatment unit 6. In this arrangement, the mixing nozzle is preferably used in reactor 1, in which toluene is nitrated to yield mononitrotoluene), and in reactor 2 in which mononitrotoluene is nitrated to yield dinitrotoluene).

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLE

The nitration of toluene to give dinitrotoluene was performed according to the present invention in an experimental plant in which the flow is as illustrated in FIG. 2. A mixture of 9.4 wt. % of nitric acid, 71.5 wt. % of sulfuric acid and 19.1 wt. % of water was used as the nitrating acid. A stream of 5000 kg/h of toluene was mixed with a stream of 36,616 kg/h of premixed nitrating acid in the mixing nozzle illustrated in FIG. 1. The average rate of flow of toluene in the tubular reactor in the mixing nozzle was 5 m/s. The average rate of flow of the nitrating acid in the annular gap in the mixing nozzle was 2.2 m/s. Nitration takes place in reactor 1 with a cooling water temperature of about 35° C., and in reactor 2 with a cooling water temperature of 65° C. The mixing nozzle is used in reactor 1.

In the comparative example, (i.e. the example not represent of the present invention) the nitrating acid and toluene are supplied to the reactor in the same ratio, but without being mixed together.

Then, the content of organic carbon in the waste water is determined by means of an analyser for organic carbon (using, for example, a model 6800 supplied by Tonics Inc.). After installing the mixing nozzle in reactor 1, a reduction of 15% in the organic carbon content in the waste water is recorded.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

The invention claimed is:

1. A process for the isothermal nitration of aromatic organic compounds, comprising
    (A) contacting (1) an aromatic organic compound, with (2) a mixture of (a) sulfuric acid and (b) nitric acid, via a mixing nozzle which comprises a substantially cylindrical tubular reactor and an annular gap surrounding the cylindrical tubular reactor, in which (1) said aromatic organic compound flows through the tubular reactor, and (2) said mixture of (a) sulfuric acid and (b) nitric acid flows through the annular gap, and (1) and (2) are mixed together upon emerging from the tubular reactor and the annular gap, wherein the ratio of the average rates of flow of (1) aromatic organic compound in the tubular reactor and of (2) the mixture of (a) sulfuric acid and (b) nitric acid in the annular gap ranges from about 0.5:1 to about 10:1; and
    (B) reacting the mixture of (1) said aromatic organic compound, and (2) said mixture of (a) sulfuric acid and (b) nitric acid, thereby forming nitrated aromatic organic compounds.

2. The process of claim 1, wherein (1) said aromatic organic compound is selected from the group consisting of benzene, toluene, phenol, mononitrotoluene and mixtures thereof.

3. The process of claim 1, wherein (1) said aromatic organic compound, and (2) said mixture of (a) sulfuric acid and (b) nitric acid flow through the mixing nozzle at a speed of 0.3 to 10 m/s.

4. The process of claim 1, wherein (1) said aromatic organic compound as it passes through the tubular reactor, and/or (2) said mixture of (a) sulfuric acid and (b) nitric acid as it passes through the annular gap, is set in rotation motion by fixed internal fittings.

5. The process of claim 1, wherein the mixture of (1) said aromatic organic compound, and (2) said mixture of (a) sulfuric acid and (b) nitric acid, emerges from the mixing nozzle with a conical flow profile.

\* \* \* \* \*